United States Patent [19]

Oinuma et al.

[11] Patent Number: 4,605,003
[45] Date of Patent: Aug. 12, 1986

[54] LITHOTRIPTOR

[75] Inventors: Senzo Oinuma; Kazumi Tanaka; Kazuo Shiino, all of Ibaraki; Hiroki Watanabe, Otsu, all of Japan

[73] Assignees: Agency of Industrial Science & Technology; Kyoto Prefectural Government; Hosoya Fireworks Co., Ltd., all of Japan

[21] Appl. No.: 676,360

[22] Filed: Nov. 29, 1984

[30] Foreign Application Priority Data

Jul. 3, 1984 [JP] Japan .................................. 59-138150

[51] Int. Cl.⁴ .............................................. A61B 17/00
[52] U.S. Cl. ......................................... 128/328; 128/7
[58] Field of Search .................... 128/328, 7; 102/530, 102/531; D24/60

[56] References Cited

U.S. PATENT DOCUMENTS 3,413,976  12/1968  Roze ..................................... D24/60
3,785,382  1/1974   Schuy et al. ......................... 128/328
4,196,736  4/1980   Watanabe ............................. 128/328

FOREIGN PATENT DOCUMENTS 1259503  6/1968  Fed. Rep. of Germany ...... 128/328

Primary Examiner—Gene Mancene
Assistant Examiner—John G. Weiss
Attorney, Agent, or Firm—Armstrong, Nikaido, Marmelstein & Kubovcik

[57] ABSTRACT

A lithotriptor is disclosed, which comprises an outer slender tube having an outside diameter small enough to be inserted into the organ growing a stone therein and an inner member disposed inside the outer slender tube. The inner member or the outer slender member incorporates therein an explosive layer or a gas-generating layer, ignition means for igniting the explosive layer or the gas-generating layer, and a closing member for preventing rearward advance of the gas evolved during the explosion of the explosive layer or the gas-generating layer. By the blasting of the explosive layer or the gas-generating layer, the outer slender tube or the inner member is caused to collide with the stone and crush it.

14 Claims, 7 Drawing Figures

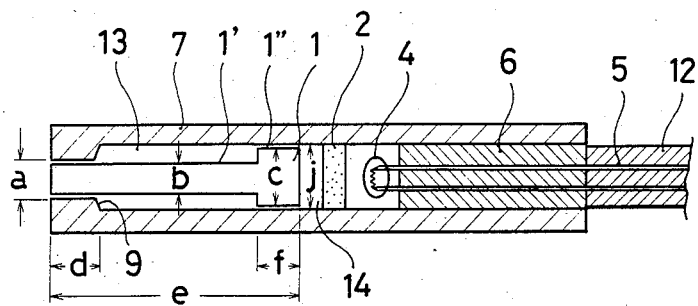
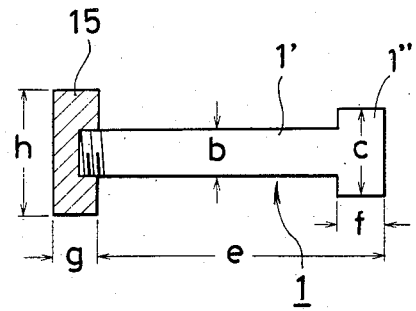
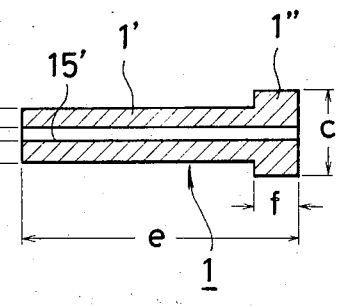
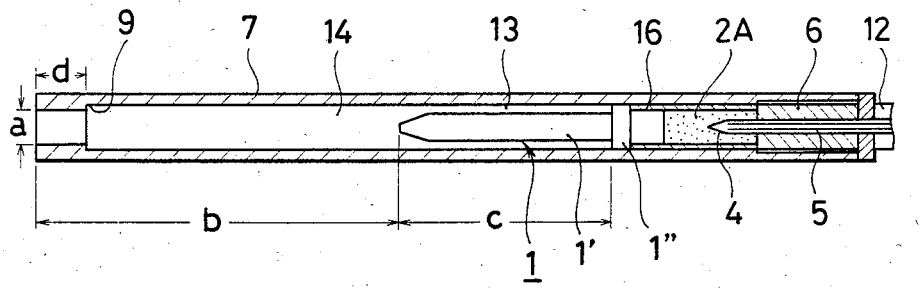

LITHOTRIPTOR

BACKGROUND

This invention relates to a lithotriptor to be used for crushing a stone in the organ of a living body.

For the destruction of a stone growing in the organ of a living body, the technique of detonating an explosive near the stone and causing the shock wave generated by the explosion to act directly upon the stone and crush it into pieces has been known to the art. Indeed this conventional method is capable of concentrating the shock wave enough to obtain effective crushing of the stone, but there is the possibility that the gas evolved by the explosion and expanded rapidly will affect the vicinity of the explosion and the crushed fragments of the stone will be sent flying in all directions by the force of the gas to inflict damage to the living tissues in the vicinity. This technique, therefore, has a serious disadvantage that its application is restrained only within internal organs having large cavities.

An object of this invention is to provide a lithotriptor such that the gas evolved and rapidly expanded by explosion of an explosive will not exert any effect upon the vicinity and will not inflict any damage to the living tissues.

Another object of this invention is to provide a lithotriptor capable of producing a large breaking force upon the stone.

Yet another object of this invention is to provide a lithotriptor which is simple in construction and easy to fabricate, and which enjoys high reliability and safety of operation.

Other objects and advantages of this invention will become apparent from the following description of the invention.

SUMMARY

For the purpose of attaining the objects described above, this invention provides a lithotriptor which comprises an outer slender tube small in outside diameter enough for insertion into the internal organ growing a stone therein and open in the leading end thereof and an inner member internally disposed in the front portion of the outer slender tube, the outer slender tube accommodating therein behind the inner member an explosive layer or a gas-generating layer, ignition means for igniting the explosive layer or the gas-generating layer, and a closing member for preventing rearward advance of the gas generated on explosion of the explosive layer or the gas-generating layer, and the closing member admitting insertion of a power feed line for passing electric current to the ignition means and thereby causing the explosive layer or gas-generating layer to explode.

For the same purpose, this invention further provides a lithotriptor which comprises an outer slender tube small in outside diameter enough to be inserted into the organ growing a stone therein and an inner member internally disposed within the outer slender tube, the outer slender tube admitting therein a flexible tube slidably inserted therein through the rear end of the outer slender tube and the rear end for insertion of the flexible tube communicating with the rear end of the inner member, the outer slender tube and the inner member consequently being displaceable in the axial direction relative to each other, the inner member accommodating therein an explosive layer, ignition means for igniting the explosive layer, and a closing member for preventing rearward advance of the gas evolved on explosion of the explosive layer, the closing member and the flexible tube admitting insertion of a power feed line for passing electric current to the ignition means thereby causing the explosion of the explosive layer, and the inner member being provided at the leading end thereof with a thin film adapted to break itself on exposure to the explosion of the explosive layer and form an opening in the inner member.

THE DRAWINGS

FIG. 1 is a cross section illustrating a typical lithotriptor of a first embodiment of the present invention;

FIG. 2 and FIG. 3 are cross sections illustrating dissimilar modifications of the inner member of the lithotriptor of FIG. 1;

FIG. 4 is a cross section illustrating a lithotriptor of a second embodiment of this invention;

THE PREFERRED EMBODIMENTS

Figure 5:
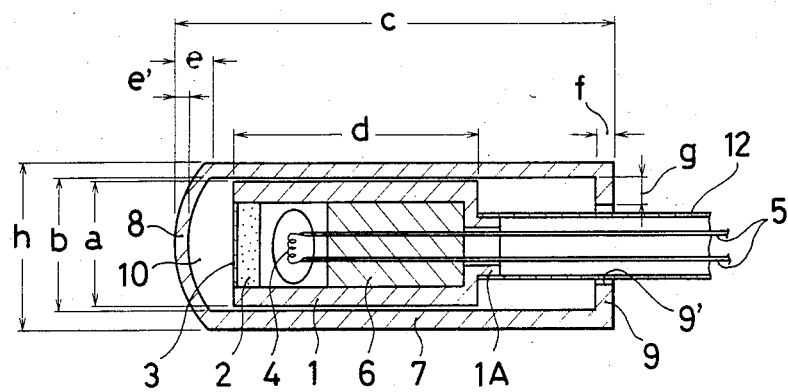
FIG. 5 is a cross section of a lithotriptor of a third embodiment of this invention.

Now, embodiments of this invention will be described below with reference to the accompanying drawings.

In the first embodiment of FIG. 1, an outer slender tube 7 which is generally formed with such metal as stainless steel or brass has an opening at the leading end thereof and has formed therein an accommodation chamber 13 for admitting axially displaceably an inner member 1 which will be described more fully afterward. The outer slender tube 7 has the rear end thereof closed with a closing member 6.

In the rear part of the accommodating chamber is disposed an explosive layer 2. To the explosive layer 2 is juxtaposed ignition means or an ignitor 4 for igniting the explosive layer 2. The ignition means 4 is provided with a power feed line 5 which is inserted through and drawn out of the closing member 6. By having this power feed line 5 connected to a power source (not shown), the ignition means 4 is caused to generate heat and explode the explosive layer 2.

In the forward part of the accommodating chamber 13 is formed a check flange 9 for preventing the inner member 1 from completely coming out of the outer slender tube 7 in consequence of the axial displacement relative to the outer slender tube 7.

The inner member 1 is composed of a first part 1' so shaped as to pierce through the stop flange 9 and thrust out of the outer slender tube 7 to a fixed length and a second part 1" so shaped as to retain intimate contact over a fixed length with the inner wall of the outer slender tube 7 and not to pierce through the stop flange 9. In the illustrated embodiment, the accommodating room 13 is so constructed as to possess one and the same diameter j at every cross section taken perpendicularly to the axis of the outer slender tube 7, and the stop flange 9 is radially raised inwardly to form an annular stop part. The first part 1' of the inner member 1 possesses a diameter b slightly smaller than the diameter a of the stop flange 9 and the second part 1" possesses a diameter c slightly larger than the diameter a and minimally smaller than the diameter j. Consequently, the inner member 1 admitted in the accommodating chamber 13 is rendered displaceable in the axial direction of the outer slender tube 7 and is allowed to thrust out of the front end of the outer slender tube 7 over a length (e-d-f). Because of the engagement between the stop flange 9 and the second part 1″, the first part is not allowed to thrust out any further.

Owing to the construction described above, the inner member 1 is moved at a high speed by explosion of the explosive layer 2 and is stopped after it has been thrust out of the leading end of the outer slender tube over a fixed distance because the rear part thereof (second part 1″) is caught by the narrow stop flange 9 of the outer slender tube 7. The rear end of the outer slender tube 7 is closed with the closing member 6 so that the gas evolved by the explosion of the explosive layer 2 will not escape through the rear end. During the explosion, the gas from the explosion does not leak outwardly because the second part 1″ of the inner member 1 stops the opening in the forward part of the slender tube. A gap 14 is formed between the inner member 1 and the explosive layer 2. This gap serves to prevent the inner member 1 from being broken by the explosion of the explosive layer 2. It may be omitted where the inner member 1 is sturdy or the explosive used has no highly destructive force. Depending on the kind of the explosive to be used, the ignitor 4 may be omitted and replaced by a setup adapted to permit direct electrical ignition.

The inner member described above is desired to be made of a tenacious material so that it will not be fractured or deformed on exposure to the impact of the explosion of the explosive or the impact due to the collision of the leading end of the inner member against the hard stone. A suitable choice of the material, therefore, may be made from among iron, brass, stainless steel, and other similar alloys. Further, the shape of the inner member 1 may be suitably selected, depending on the shape, size, hardness, etc. of the stone to be removed. FIG. 2 illustrates an inner member of the type having a colliding part 15 at least equal to or longer than in outside diameter to the outer slender tube 7 secured as by means of a screw to the small leading end of the inner member 1. This inner member suits the crushing of a rather large flat stone because the colliding part 15 serves to increase the area of collision against the stone. FIG. 3 depicts an inner member of the type having a through hole 15′ formed along the axis thereof throughout the entire length from the leading end to the rear end. This inner member is effectively used where the stone is large and the organ is judged to tolerate leakage of the gas from explosion to some extent. This inner member offers increased destructive force because the gas of explosion is spurted out of the through hole 15′ against the stone after the inner member 1 has collided against the stone.

In the lithotriptor of the first embodiment, the inner shape of the outer slender tube 7 (namely the shape of the accommodating chamber 13) and the shape of the stop flange may be varied. These shapes are freely selected on the sole, essential condition that the forward part of the inner member 1 is allowed to be thrust out over the prescribed length by the explosion of the explosive layer 2 and the gas from explosion is prevented from undesired leakage.

Now, experiments performed on lithotriptors of the first embodiment described above used for actual removal of stones will be cited below by way of illustration.

Experiment 1

With reference to the construction of FIG. 1, in an outer slender tube 7 of stainless steel measuring 3 mm in outside diameter, 2 mm in inside diameter, and 20 mm in length and having dimensions of 1.5 mm as the leading end a and 2 mm as the size of d, an inner member 1 of brass having dimensions of 1.4 mm at b, 1.95 mm at c, 9 mm at e, and 2 mm at f was inserted and, as an explosive layer 2, 8 mg of a mixture of 95% of DDNP and 5% of nitrocellulose was placed behind the inner member, with ignition means 4 held in contact with the explosive layer 2 and a power feed line 5 for the ignition means extended through the outer slender tube 7 and led out of the rear end thereof. The rear opening of the outer slender tube 7 was closed with a closing member 6 made of epoxy resin.

The leading end of the outer slender tube 7 of the lithotriptor constructed as described above was brought into contact with an artificial stone prepared preponderantly of gypsum in diameter of 23 mm with compressive strength of 130 kg/cm$^2$ and placed in a porcine bladder immersed in water and then the power feed line 5 was connected to a power source to ignite the explosive layer 2. Consequently, the inner member 1 flew through the leading end of the outer slender tube 7 and stopped at a distance of 5 mm. The artificial stone was broken into five smaller fragments. The porcine bladder, by visual examination, was found to have sustained no damage.

Experiment 2

The procedure of Experiment 1 was repeated by using a lithotriptor similar in construction to the lithotriptor of Experiment 1, except that an inner member 1 of brass in a shape of FIG. 2 having dimensions of 1.4 mm at b, 1.95 mm at c, 9 mm at e, 2 mm at f, 3 mm at h, and 1.5 mm at g was used instead. An artificial stone 26 mm in diameter used in this experiment could be broken into six smaller fragments. The porcine bladder was found to sustain no discernible damage.

Experiment 3

The procedure of Experiment 1 was repeated by using a lithotriptor similar in construction to the lithotriptor of Experiment 1, except that an inner member of brass in a shape of FIG. 3 having dimensions of 1.4 mm at b, 1.95 mm at c, 9 mm at e, 2 mm at f, and 0.7 mm at i was used instead. An artificial stone, 27 mm in diameter, could be broken into 10 smaller fragments. The porcine bladder was found to sustain no discernible damage.

Experiment 4

With reference to the construction of FIG. 1, in an outer slender tube 7 measuring 2 mm in outside diameter, 1.5 mm in inside diameter, and 14 mm in length and having dimensions of 1.1 mm as a leading end a and 2 mm as the size of d, an inner member 1 of stainless steel having dimensions of 1.0 mm at b, 1.45 mm at c, 7 mm at e, and 1 mm at f was inserted and an explosive layer 2 formed of 3 mg of tricinate was placed behind the inner member 1 and a platinum bridge welded to the leading end of a power feed line 5 was set in place in contact with the explosive layer 2, with the power feed line 5 extended through the outer slender tube 7 and led out of the rear end of the outer slender tube 7. The opening at the rear end of the outer slender tube was closed with a closing member 6 of epoxy resin.

Then, the leading end of the outer slender tube 7 of the lithotriptor thus formed was inserted into a porcine ureter and brought into contact with a human ureter stone, 9 mm in diameter, and the power feed line 5 was connected to a power source to ignite the explosive layer 2. Consequently, the inner member 1 flew out of the leading end of the outer slender tube 7 and stopped at a distance of 4 mm. The stone was broken into 6 smaller fragments. The ureter was not found to have sustained any discernible damage.

The lithotriptor of the second embodiment of this invention illustrated in FIG. 4 is roughly similar in construction to the lithotriptor of the first embodiment of FIG. 1. Thus, like parts are denoted by like numeral symbols. The difference between the two lithotriptors resides in the fact that a gas-generating layer 2A is disposed in place of the explosive layer 2 behind the accommodating chamber 13 and ignition means 4 for igniting the gas-generating layer 2A is juxtaposed to the gas-generating layer 2A. The ignition means 4 is inserted through the closing member 6 and led out of the outer slender tube by means of the power feed line 5. By connecting the power feed line 5 to its power source, the ignition means 4 is caused to generate heat and ignite the gas-generating layer 2A.

By the combustion of the gas-generating layer 2A, the inner member 1 is moved at a high speed. As the opening is held in direct contact with the stone, the leading end of the inner member collides against the stone after the inner member has been accelerated to a high velocity while in motion over a distance b. The first part 1' is allowed to thrust out of the leading end of the opening over a distance of c-d. It is stopped and prevented from being thrust out any further because of the engagement between the stop flange 9 and the second part 1". Of course, the crushing force exerted upon the stone is affected by the amount of the gas-generating layer 2A to be used and yet is heavily varied by the length of the empty part 14, namely the distance over which the inner member 1 is accelerated in motion. Thus, the length of the empty part 14 may be suitably determined, depending on the amount of the gas-generating layer 2A and the weight of the inner member 1. The ignition means 4, depending on the kind of the gas-generating layer 2A, may be of a type for providing direct electrical ignition. Some other suitable ignition means may be used when desired.

The gas-generating layer 2A to be used in the lithotriptor constructed as described above can be formed of black powder or smokeless powder generally used as a propellant or a small amount of explosive or initiator such as tricinate, DDNP, or lead azide not enough to release shock wave outwardly. Otherwise, the gas-generating layer 2A may incorporate therein an organic compound capable of adjusting the rate of detonation of the initiator or increasing the amount of gas evolved.

Factors which substantially govern the destructive force of the lithotriptor are the kind and the amount of the gas-generating layer 2A to be used. The length of the empty part 14, namely the distance over which the inner member 1 is accelerated in motion, can also be cited as a contributory factor.

For the enhancement of the destructive force of the lithotriptor, therefore, the empty part 14 is desired to have a length (generally in the range of 3 to 7 mm) which suits the kind and the amount of the gas-generating layer 2A and the weight of the inner member 1.

Now, experiments performed on lithotriptors of the second embodiment described above as used for actual destruction of stones will be cited below by way of illustration.

Experiment 1

With reference to the construction of FIG. 4, in an outer slender tube 7 of stainless steel measuring 3 mm in outside diameter, 2 mm in inside diameter, and 22 mm in length and having dimensions of 1.5 mm as the leading part a and 2 mm as the size of d, an inner member 1 of brass having dimensions of 1.4 mm and 1.95 mm respectively as the diameters of 2' and 2" and 7 mm as the size of c was inserted so as to provide an empty part b of 5 mm in length. As a gas-generating layer 2A for propulsion, 8 mg of a mixture consisting of 95% of DDNP and 5% of nitrocellulose was placed behind the inner member 1. The rear part of the inner member 1 was fitted to one end of a container tube 16 for the gas-generating agent, the gas-generating layer 2A was set in place, and the ignition means 4 for electrical ignition was inserted and fixed in place. Adhesive agent was applied on the outer periphery of the container tube 16 and the container tube 16 was inserted in the outer slender tube 7. Subsequently, the power feed line 5 for the ignition means 4 was coated with adhesive agent and led out of the closing member 6 made of epoxy resin. At the same time, the closing member 6 was closed by being helically fitted into the outer slender tube 7 of stainless steel.

For comparison, a lithotriptor was fabricated in construction identical with the construction of the lithotriptor just described above, except that the size of b was reduced to 0 mm, i.e. no empty part 14 was provided between the leading end of the inner member 1 and the opening of the outer slender tube.

Then, the leading end of the outer slender tube 7 of each of the lithotriptor of the second embodiment and that for the comparison was brought into contact with an artificial stone prepared preponderantly of gypsum in diameter of 23 mm with compression strength of 130 kg/cm$^2$ and set in place in a porcine bladder immersed in water and the power feed line 5 was connected to its power source to ignite the gas-generating layer 2A. In the lithotriptor of the second embodiment, the inner member 1 was severed from the container tube 16 and thrust out of the leading end of the outer slender tube 7 and stopped at a distance of 5 mm. The artificial stone was broken into 5 smaller fragments. In this case, the porcine bladder was found to have sustained no discernible damage. In the lithotriptor of the comparison, the inner member 1 was similarly thrust out of the leading end of the outer slender tube 7 and stopped at a distance of 5 mm. The artificial stone was broken into two pieces along the portion at which the leading end of the inner member 1 collided against the artificial stone.

According to the results of the experiments cited above, the lithotriptor of the present invention has a salient advantage that the gas evolved and quickly expanded by the explosion of the explosive or the gas-generating layer neither exerts any adverse effect upon the vicinity nor inflicts any damage to the living tissues and yet manifests a high destructive force upon the stone.

Because of the construction described above, either of the outer slender tube and the inner member inserted axially displaceably within the outer slender tube is enabled to function as a movable part and the other as a support part, they are mutually displaceable in the axial direction. Thus, the lithotriptor enjoys an advantage that it is simple in construction, easy to fabricate and reliable and safe in operation.

Now, the third embodiment of this invention illustrated in FIG. 5 will be described below. A tubular inner member 1 formed of such metal as stainless steel has an explosive layer 2 filling an opening at the leading end thereof. Behind the explosive layer 2, ignition means 4 is disposed as juxtaposed thereto. A thin film 3 of synthetic resin which covers the front end face of the explosive layer 2 serves to prevent the explosive layer 2 from falling off the inner member 1 and protect it against moisture.

A power feed line 5 feeds electric current to the ignition means 4 and causes the explosion of the explosive layer 2. Denoted by 6 is a closing member which fills up the rear half part of the inner member 1 for the purpose of preventing rearward advance of the gas evolved when the explosive layer 2 is exploded by the ignition means 4. A connection mouth 1A is integrally formed at the rear end of the inner member 1. A flexible tube 12 is connected to the connection mouth 1A and possesses a length enough to permit insertion of the lithotriptor into the organ. Through this flexible tube 12 is inserted the aforementioned power feed line 5 and constitutes itself one of the component members of the lithotriptor.

The power feed line 5 for the ignition means 4 is passed through the closing member 6 inside the inner member 1, further sent through the flexible tube 12, and led out of the flexible tube 12 to be connected to a power source (not shown in the diagram) via a suitable switch.

In addition to functioning as protective means for the power feed line 5, the flexible tube 12 serves as operating means for the insertion of the lithotriptor into the organ and as means for stationarily retaining the inner member 1 during explosion of the explosive layer 2.

The slender tubular inner member 1 incorporating therein the explosive layer 2, the ignition means 4, and the closing member 6, and the power feed line 5 and the flexible tube 12 jointly form a support member of a one-piece structure relative to the movable part to be described more fully afterward in the lithotriptor of the present invention.

An outer slender tube 7 wraps itself tightly around the outer periphery of the inner member 1 of the aforementioned support member and, thus, incorporates the inner member 1 axially displaceably (in the direction of length) therein. The leading end of the outer slender tube 7, namely the end corresponding in the axial direction to the front end opening of the inner member 1 filled up by the explosive layer 2, is closed with an end wall 8 in the first embodiment of FIG. 1. The outer slender tube 7 is provided at the rear end thereof with a stop flange 9. The end wall 8 and the stop flange 9 may be formed integrally with the outer slender tube 7. Otherwise, they may be separately formed and subsequently attached fast thereto as by welding. They may be in any desired shape so long as they function as stop parts for preventing otherwise possible separation of the inner member 1 from the outer slender tube 7 in consequence of the axial displacement of the inner member 11.

The outer slender tube 7, the end wall 8, and the stop flange 9 form a movable member of a one-piece construction relative to the aforementioned support member.

The outside diameter h of the outer slender tube 7 is selected so as to permit the lithotriptor to be inserted into the organ in which the stone is present. The inside diameter of the outer slender tube 7 is slightly larger than the outside diameter a of the inner member 1. The length c of the outer slender tube 7 is selected to be fairly greater than the length d of the inner member 1. Consequently, while the movable member completely embraces the inner member 1 of the support member, the flexible tube 12 of the support member is led outwardly (backwardly) through the central hole 9' of the stop flange 9 of the movable member.

Figure 6:
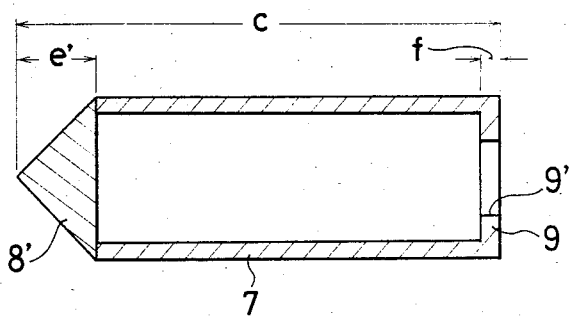
FIG. 6 is a cross section of the outer slender tube of the lithotriptor of the third embodiment of this invention.
Figure 7:
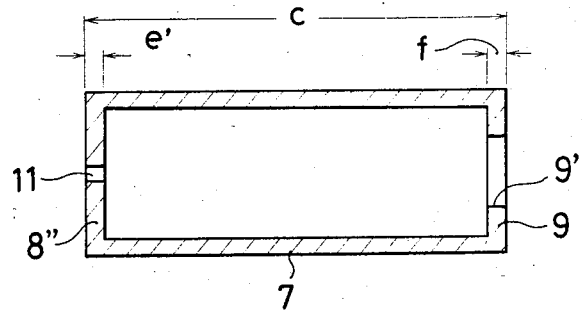
FIG. 7 is a cross section of a modification of the outer slender tube of the lithotriptor of the third embodiment of this invention.

The movable member is axially displaceable relative to the support member within the range of the length c thereof minus the sum of the length d of the inner member 1, the bulge e of the end wall 8 (thickness e' in FIG. 6 and FIG. 7), and the thickness f of the stop flange 9, thus $c - (d + e \text{ or } e' + f)$.

As the explosive layer 2 is exploded by the ignition means 4, the movable member is displaced forwardly at a high speed relative to the support member by the pressure of the gas evolved by the explosion and the outer surface of the end wall 8 collides against the stone and crushes it. Since the stop flange 9 at the rear end is stopped by the rear end of the inner member 1 of the support member, the movable member is brought to a forced stop after it has been moved over a fixed distance within the aforementioned length of displacement. The movable member, therefore, will not come off the support member under any condition. At the moment that the movable member is stopped as described above, the inner end face of the stop flange 9 is powerfully pressed against the rear end face of the inner member 1 by the pressure of the explosion of the explosive layer 2. Consequently, the gas evolved by the explosion will not leak out of the lithotriptor through the interface between the outer peripheral surface of the inner member 1 and the inner wall surface of the outer slender tube 7.

Optionally, an empty space 10 may be formed in advance as illustrated in FIG. 5 between the end wall 8 of the outer slender tube 7 of the movable member and the thin film 3 on the surface of the explosive layer 2 of the inner member 1 of the support member so as to prevent the end wall 8 from possible breakage by the explosion of the explosive layer 2. This empty space 10 may be eliminated by fabricating the end wall 8 with ample tenacity or by properly selecting the kind of the explosive to be used. Depending on the kind of the explosive to be used, the ignition means 4 need not be disposed behind the explosive layer 2. It may be buried in the explosive layer 2 and directly activated by electricity or laser to ignite the explosive layer 2.

The explosive layer for use in the lithotriptor of the third embodiment is formed of a small amount of a detonator or initiator such as, for example, tricinate, DDNP or lead azide not enough to inflict any damage upon the movable member. Optionally, the explosive layer may incorporate therein an organic compound capable of adjusting the detonation velocity of the initiator or increasing the amount of the gas evolved by the explosion.

The movable member in the lithotriptor of the third embodiment is required to be formed of sturdy material such that the movable member will be neither deformed nor broken on exposure to the impact of the explosion or the impact produced when the end wall 8 collides against a hard stone. A good choice of the material, therefore, may be made from among iron, brass, stainless steel, and other similar alloys. The shape of the movable member, particularly the end wall 8, can be suitably selected depending on the shape, size, strength, etc. of the stone. For example, as in the modification of the second embodiment illustrated in FIG. 6, the end wall 8 may be formed in the shape of a cone pointed toward the front, so that the leading end of this cone will be utilized effectively in the crushing of the stone. In the modification of the third embodiment illustrated in FIG. 7, a through hole 11 may be formed in the end wall 8" of the movable member so that the gas of the explosion will be spurted through the through hole 11 at the same time that the movable member is hurled against the stone. Thus, the lithotriptor provides an enhanced destructive force. This lithotriptor, therefore, can be used effectively where the stone is large or where the organ is judged to tolerate leakage of the gas of explosion to some extent.

Now, experiments performed on lithotriptors of the third embodiment described above as used for actual destruction of stones will be cited below by way of illustration.

Experiment 1

With reference to the construction of FIG. 5, an inner member 1 was made of stainless steel in dimensions of 2 mm as the outside diameter a and 20 mm as the length d, and an outer slender tube 7 of the movable member was made of stainless steel in dimensions of 2.05 mm as the inside diameter b, 35 mm as the length c, 2 mm as the thickness e' of an end wall 8, 2 mm as the thickness f of a stop flange 9, and 2 mm as the width g in the radial direction of the stop flange 9. The movable member was wrapped around the inner member 1. Then, 5 mg of lead azide was used to form an explosive layer 2, platinum bridge was used as ignition means 4, and epoxy resin was used to form a closing member 6.

Then, an artificial stone formed of a mixture of gypsum with emery in a diameter of 30 mm with compressive strength of 120 kg/cm$^2$ was suspended in water. The outer surface of the end wall 8 of the movable member of the lithotriptor constructed as described above was brought into contact with one end of the artificial stone. By feeding DC of 3 V to the power feed line 5, the igniting means 4 was activated to explode the explosive layer 2. Consequently, the movable member was urged at a high speed and stopped at a distance of about 10 mm, and the end wall 8 delivered a hard strike to the artificial stone and crushed it into about 10 small fragments. In this case, the gas evolved by the explosion did not leak out of the lithotriptor at all. The impact of the explosion neither fractured nor punctured the inner member 1 or the movable member.

Experiment 2

A lithotriptor was fabricated in the same construction as obtained in Experiment 1. A stone 10 mm × 15 mm in outside diameters taken out from the ureter of a human subject was inserted in a porcine ureter removed from a sacrificed swine and immersed in water. The lithotriptor was inserted into the porcine ureter via one end thereof and the outer surface of the end wall 8 was brought into contact with one end of the stone and the explosive layer 2 was exploded by following the procedure of Experiment 1. Similarly to Experiment 1, the movable member was urged at a high speed and then stopped, and the end wall 8 delivered a powerful strike to the stone and crushed it. In this case, the inner member 1 and the movable member sustained no breakage due to fracture or puncture. The porcine ureter was found to have underwent no discernible change.

Experiment 3

A lithotripter was fabricated in the same construction as in Experiment 1. A stone 22 mm × 31 mm in outside diameter excised from the kidney of a human subject was concealed in a porcine renal pelvis removed from a sacrificed swine and the cut formed in the porcine renal pelvis for the concealment of the stone was sutured. The porcine renal pelvis was immersed in water. The lithotriptor was inserted into the porcine renal pelvis through the severed end of the porcine ureter which continued into the porcine renal pelvis and the outer surface of the end wall 8 was brought into contact with one end of the stone. Then, by following the procedure of Experiment 1, the explosive layer 2 was exploded. Consequently, the movable member was moved at a high speed and stopped, and the end wall 8 delivered a powerful strike to the stone and crushed it. In this case, the inner member 1 and the movable member sustained no breakage due to fracture or puncture. No discernible change was observed on the porcine kidney, the porcine renal pelvis, or the porcine ureter.

The lithotriptors of Experiments 1, 2, and 3 described above are invariably constructed so that the explosive layer 2 disposed in the inner member 1 as the support member inside the outer slender tube 7 of the shape of a capsule as the movable member and, with the gas evolved by the resultant explosion utilized as the driving energy, the movable member on the outside is caused to move at a high speed in the axial direction relative to the support member on the inside, and the front end surface of the movable member is caused to collide against the stone and crush it. The movable member is stopped after it has been urged over a prescribed distance.

Since the explosion of the explosive layer 2 is effected within the movable member of the shape of a capsule, the adverse effect of the gas of explosion upon the surrounding tissues can be substantially eliminated. The movable member is stopped without fail by the support member after it has travelled a prescribed distance relative to the support member. Thus, there is absolutely no possibility of the movable member colliding against the surrounding tissues and inflicting damage upon them. Since the movable member falls outside the support member, the length of the movable member in the axial direction and the thickness of the end wall 8 have ample freedom of selection. Thus, the lithotriptor can be designed by selecting the aforementioned length and width so that the movable member will be enabled to manifest its kinetic energy most efficiently. When the mass of the movable member is increased, the strength of the stop flange 9 of the movable member relative to the support member can be increased proportionately to the increase in mass. Thus, accidental departure of the movable member from the support member can be prevented from occurring with perfect certainty.

Further, by suitably altering the shape of the end wall 8 of the movable member, the condition of contact between the stone and the end wall 8 can be optimized for the purpose of crushing the stone. Since the movable member and the support member are both simple in construction, the lithotriptor can be manufactured easily.

By the use of the lithotriptor of the third embodiment, stone occurring in narrow organs such as stone in the ureter and large stones occurring as closely adhering to surrounding tissues such as stone in the renal pelvis can be completely crushed with ample energy.

We claim:

1. A lithotriptor comprising an outer slender tube small in outside diamter enough for insertion into an organ growing a stone therein and open in the leading end thereof, an inner member internally disposed in the front portion of said outer slender tube, means for preventing gases from leaving said outer slender tube, said outer slender tube accommodating therein behind said inner member an explosive layer or a gas-generating layer, ignition means for igniting said explosive layer or said gas-generating layer, and a closing member for preventing rearward advance of the gas generated on explosion of said explosive layer or said gas-generated layer, and said closing member admitting insertion of a power feed line for passing electric current to said ignition means and thereby causing explosion of said explosive layer of gas-generating layer.

2. A lithotriptor according to claim 1, wherein said outer slender tube is provided at the front end thereof with an annular stop part raised inwardly in the radial direction from said outer slender tube and adapted to prevent said inner member from coming out of said outer slender tube in consequence of displacement thereof in the axial direction and said inner member is composed of a first part having a diameter slightly smaller than the diameter of said stop part and disposed at the forward side of said inner member and a second part having a diameter larger than the diameter of said stop part and smaller than the inside diameter of said outer slender tube and disposed at the rearward portion of said inner member.

3. A lithotriptor according to claim 1 or claim 2, wherein said explosive layer, said ignition means, and said closing member are sequentially disposed as mutually juxtaposed from the forward to the rearward end.

4. A lithotriptor according to claim 1 or claim 2, wherein said ignition means is buried in said explosive layer.

5. A lithotriptor according to any of claims 1 or 2, wherein an empty part is interposed between the rear end of said inner member and said explosive layer or said gas-generating layer.

6. A lithotriptor according to any of claims 1 or 2, wherein said inner member is provided at the leading end thereof with a colliding part having an outside diameter larger than the outside diameter of said outer slender tube.

7. A lithotriptor according to any of claims 1 or 2 wherein said inner member has a through hole formed along the axis thereof throughout the entire length from the leading end to the rear end.

8. A lithotriptor, comprising an outer slender tube small in outside diamter enough to be inserted into an organ growing a stone therein and an inner member internally disposed within said outer slender tube, said outer slender tube admitting therein a flexible tube slidably inserted therein through the rear end of said outer slender tube and communicating with said inner member, said outer slender tube and said inner member consequently being displaceable in the axial direction relative to each other, said inner member accommodating therein an explosive layer, ignition means for igniting said explosive layer, and a closing member for preventing rearward advance of the gas evolved on explosion of said explosive layer, said closing member and said flexible tube admitting insertion of a power feed line for passing electric current to said ignition means thereby causing explosion of said explosive layer, and said inner member being provided at the leading end thereof with a thin film adapted to break itself on exposure to the explosion of said explosive layer and form an opening in said inner member.

9. A lithotriptor according to claim 8, wherein said outer slender tube has an end wall at its distal end which is converged in the forward direction in the shape of a cone.

10. A lithotriptor according to claim 8, wherein said outer slender tube has an opening at its front end.

11. A lithotriptor according to any of claims 8 through 10, wherein said explosive layer, said ignition means, and said closing member are sequentially disposed as mutually juxtaposed from the forward to the rearward end.

12. A lithotriptor according to any of claims 8 through 10, wherein said ignition means is buried in said explosive layer.

13. A lithotriptor according to any of claims 8 through 10, wherein an empty part is interposed between the front end of said outer slender tube and the front end of said inner member.

14. A lithotriptor according to any of claims 8 through 10, wherein said outer slender tube is provided at the rear end thereof with a stop part for preventing said inner member from coming off said outer slender tube in consequence of axial displacement thereof and said flexible tube is inserted slidably into said outer slender tube through the medium of said stop part.

* * * * *